(12) United States Patent
De Waele et al.

(10) Patent No.: US 11,207,049 B2
(45) Date of Patent: *Dec. 28, 2021

(54) SYSTEM AND METHOD FOR CHARACTERIZING AN UPPER AIRWAY USING SPEECH CHARACTERISTICS

(71) Applicant: KONINKLIJKE PHILIPS N.V., Eindhoven (NL)

(72) Inventors: Stijn De Waele, Milwood, NY (US); Stefan Winter, Würselen (DE); Alexander Cornelis Geerlings, Boxmeer (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 345 days.

This patent is subject to a terminal disclaimer.

(21) Appl. No.: 16/253,003

(22) Filed: Jan. 21, 2019

(65) Prior Publication Data

US 2019/0150879 A1    May 23, 2019

Related U.S. Application Data (63) Continuation of application No. 14/352,336, filed as application No. PCT/IB2012/055501 on Oct. 11, 2012, now Pat. No. 10,182,787.

(Continued)

(51) Int. Cl.
*A61B 7/00*    (2006.01)
*C03B 33/07*    (2006.01)
(Continued)

(52) U.S. Cl.
CPC .......... *A61B 7/003* (2013.01); *A61B 5/0826* (2013.01); *A61B 5/1075* (2013.01);
(Continued)

(58) Field of Classification Search
CPC .............................. A61B 7/003; A61B 5/4803
See application file for complete search history.

(56) References Cited

U.S. PATENT DOCUMENTS

| | | | |
|---|---|---|---|
| 5,826,570 A | 10/1998 | Goodman et al. | |
| 6,236,963 B1 | 5/2001 | Naito et al. | |

(Continued)

FOREIGN PATENT DOCUMENTS

| | | | |
|---|---|---|---|
| CA | 2585824 A1 | 9/2008 | |
| JP | 2001249675 A | 9/2001 | |

(Continued)

OTHER PUBLICATIONS

Tanaka K, Kitajima K, Tanaka H. Relationship between Transglottal Pressure and Fundamental Frequency of Phonation, with Effects of Dehydration Produced by Atropine, in Healthy Volunteers. Annals of Otology, Rhinology & Laryngology. 2001;110(11):1066-1071. doi: 10.1177/000348940111001114 (Year: 2001).*

(Continued)

*Primary Examiner* — Daniel L Cerioni
*Assistant Examiner* — Yasmeen S Warsi (57) ABSTRACT

The present invention relates to systems and methods for characterizing at least one anatomical parameter of an upper airway of a patient by analysing spectral properties of an utterance, comprising: a mechanical coupler comprising means for restricting the jaw position of the patient; means for recording an utterance; and processing means for determining at least one anatomical parameter of the upper airway from the recorded utterance and comparing the recorded utterance to a threshold value. In addition the present invention relates to the use of the above mentioned systems as a diagnostics tool for assessing obstructive sleep apnea.

3 Claims, 4 Drawing Sheets

Related U.S. Application Data (60) Provisional application No. 61/549,345, filed on Oct. 20, 2011.

(51) Int. Cl.

| | | |
|---|---|---|
| *B26D 1/30* | (2006.01) | |
| *B26B 15/00* | (2006.01) | |
| *C03B 33/12* | (2006.01) | |
| *A61B 5/08* | (2006.01) | |
| *A61B 5/107* | (2006.01) | |
| *A61B 5/00* | (2006.01) | |
| *A61B 7/04* | (2006.01) | |
| *B26D 1/00* | (2006.01) | |
| *A61M 15/00* | (2006.01) | |
| *G10L 25/66* | (2013.01) | |
| *G10L 25/75* | (2013.01) | |

(52) U.S. Cl.
CPC ............ *A61B 5/4803* (2013.01); *A61B 5/486* (2013.01); *A61B 5/4818* (2013.01); *A61B 5/4839* (2013.01); *A61B 5/70* (2013.01); *A61B 5/7282* (2013.01); *A61B 5/749* (2013.01); *A61B 7/04* (2013.01); *B26B 15/00* (2013.01); *B26D 1/30* (2013.01); *C03B 33/07* (2013.01); *C03B 33/074* (2013.01); *C03B 33/076* (2013.01); *C03B 33/078* (2013.01); *C03B 33/12* (2013.01); *A61B 5/7267* (2013.01); *A61B 2562/0204* (2013.01); *A61M 15/00* (2013.01); *B26D 2001/006* (2013.01); *B26D 2001/0066* (2013.01); *G10L 25/66* (2013.01); *G10L 25/75* (2013.01); *Y10T 83/04* (2015.04)

(56) References Cited

U.S. PATENT DOCUMENTS

| | | |
|---|---|---|
| 6,580,944 B1 | 6/2003 | Katz et al. |
| 8,346,553 B2 | 1/2013 | Abe |
| 2004/0134496 A1 | 7/2004 | Cho et al. |
| 2004/0225226 A1 | 11/2004 | Lehrman et al. |
| 2009/0020113 A1 | 1/2009 | Watanabe |
| 2009/0285763 A1 | 11/2009 | Finlay |
| 2010/0250256 A1 | 9/2010 | Hiraishi |
| 2010/0252037 A1 | 10/2010 | Wondka et al. |
| 2010/0324417 A1 | 12/2010 | McNair |
| 2011/0071444 A1 | 3/2011 | Kassatly |
| 2011/0240015 A1 | 10/2011 | Nikander et al. |
| 2013/0297293 A1 | 11/2013 | Di Cristo et al. |
| 2014/0276228 A1 | 9/2014 | De Waele et al. |

FOREIGN PATENT DOCUMENTS

| | | | |
|---|---|---|---|
| JP | 2008026357 A | | 2/2008 |
| JP | 2008026357 A | * | 8/2008 |
| JP | 2009045446 A | | 3/2009 |

OTHER PUBLICATIONS

JP2008026357 English Translation (Year: 2008).*
Bi et al, "Clinical Significance of Acoustic Pharyngealmetry for Diagnosing Osahs", Journal of Tongji Universisty (Medical Science), vol. 27, No. 3, Jun. 2006, pp. 61-63.
Kikander et al, "Manipulation of Upper Airway Volume Using a Stepped Mouthpiece", European Respiratory Society, 2010, pp. 1-2.
Fiz, Jose A., et al. "Acoustic analysis of vowel emission in obstructive sleep apnea." Chest 104.4 (1993): 1093-1096.
Jung, D. et al., "Predictive Value of Kushida Index and Acoustic Pharyngometry for the Evaluation of Upper Airway in Subjects With or Without Obstructive Sleep Apnea", J Korean Med Sci, 2004.

* cited by examiner

SYSTEM AND METHOD FOR CHARACTERIZING AN UPPER AIRWAY USING SPEECH CHARACTERISTICS

CROSS-REFERENCE TO PRIOR APPLICATIONS

This application is a continuation application of U.S. National Phase application under 35 U.S.C. § 371, Ser. No. 14/352,336, filed on Apr. 17, 2014, which claims the benefit of International Application Serial No. PCT/IB2012/055501, filed on Oct. 11, 20112, which claims the benefit of U.S. Application Ser. No. 61/549,345, filed on Oct. 20, 2011. These applications are hereby incorporated by reference herein.

TECHNICAL FIELD OF THE INVENTION

The present invention relates to a system and method for characterizing an upper airway using speech characteristics.

BACKGROUND OF THE INVENTION

Obstructive Sleep Apnoea (OSA) is a disease whereby the upper airway is obstructed many times per night to such an extent that the patient is unable to breathe (apnoea) or has a reduced breathing capacity (hyponea). Diagnosis of OSA can be done in a sleep lab by monitoring a patient during an overnight measurement. If the total of number of apnoea's and hyponeas exceeds a certain limit, the OSA diagnosis is assigned.

Jung et al disclose that predictive indicators of OSA are the anatomical features related to the upper airway in Predictive value of Kushida index and use acoustic pharyngometry for the evaluation of upper airway in subjects with or without obstructive sleep apnoea. (J Korean Med Sci, 2004. 19(5): p. 662-7). Jung et al also disclose that the spectral characteristics of speech, notably vowels, depend on the anatomical dimensions of the throat. As a result of the latter, spectral characteristics of speech can be used as indicators for OSA. For this an acoustic pharyngometer can be used to actively extract geometric parameters of the upper airway by sending an acoustic signal into the throat and processing the reflections of the latter. However, test/retest validity and the accuracy of an acoustic pharyngometry measurement performed by devices known in the art is not that high.

CA2585824 discloses a method for screening OSA, namely to derive flow information from breathing sounds in the ear, and combine them with the level of snoring. However, the method disclosed in CA '824 can only be used to detect apnoea as they happen.

In addition, unfortunately these diagnosis tools for OSA common in the art are used in a sleep lab, which is expensive, time-consuming and uncomfortable for the patient. Furthermore, the methods at present used for screening OSA are very tedious and labour-intensive.

Therefore a need still exists for an improved and less time-consuming test for daytime investigating and screening of OSA in a short and convenient way.

SUMMARY OF THE INVENTION

It is an object of the present invention to provide a system and method for characterizing an upper airway using speech characteristics.

The above objective is accomplished by a method and system according to the present invention. Particular and preferred aspects of the invention are set out in the accompanying independent and dependent claims. Features from the dependent claims may be combined with features of the independent claims and with features of other dependent claims as appropriate and not merely as explicitly set out in the claims.

A first aspect of the invention relates to systems for characterizing at least one anatomical parameter of an upper airway of a patient by analyzing spectral properties of an utterance, the system comprising:
 a mechanical coupler comprising means for restricting the jaw position of the patient;
 means for recording an utterance; and
 processing means for determining at least one anatomical parameter of the upper airway from the recorded utterance and comparing the recorded utterance to a threshold value.

In some embodiments the characterization can be performed autonomously. The system and method according to the present invention functions independently: once the operation is started, it continues until the operation is terminated, without manual intervention, but possibly under the control of a controller. Advantageously, the system according to embodiments of the present invention can autonomously check whether that a user has preformed the required utterance.

In some embodiments the processing means provides real-time feedback. Yet in other embodiments the system further comprises means for speech recognition for controlling correctness of the recorded utterance.

In other embodiments the system further comprises means for delivering at least one respiratory drug through the upper airway of the patient.

In one embodiment of the present invention the at least one anatomical parameter is the cross-section of the upper airway and wherein the system further comprises means for determining at least one point of time when the cross-section is maximal during an utterance.

In yet another embodiment the system further comprises means for delivering at least one respiratory drug through said upper airway of the patient at said at least one point of time when said cross-section of the upper airway is maximal. In one embodiment of the present invention the respiratory drug delivering means comprises a timing mechanism.

A second aspect of the invention relates to the use of the above mentioned systems as a diagnostics tool for assessing obstructive sleep apnea.

A further aspect of the invention relates to methods for assessing at least one anatomical parameter of an upper airway of a patient by analyzing spectral properties of an utterance, comprising the steps of:
 restricting a jaw position of the patient;
 recording an utterance;
 comparing the recorded utterance with a threshold value; and
 determining the at least one anatomical parameter of the upper airway from the recorded utterance and the comparison of the recorded utterance with a threshold value.

In preferred embodiments the method further comprises the step of providing real-time feedback.

In some embodiments the method further comprises the step of adapting the patient's body position.

In other embodiments the method further comprises the step of storing the spectral properties of the recorded utterance in a database.

In yet other embodiments of the invention the threshold value is determined by means of speech recognition.

The invention according to embodiments of the invention further includes a method wherein the at least one anatomical parameter is the cross-section of said upper airway and wherein said method further comprises the step of determine at least one point of time when the cross-section is maximal when executing an utterance.

Embodiments of the invention include a method further comprising the step of delivering at least one respiratory drug in the upper airway of the patient.

The teachings of the present invention permit the design of improved methods and systems for guiding a user in performing accurate and reliable measurements for characterizing an upper airway.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

In the different figures, the same reference signs refer to the same or analogous elements.

DESCRIPTION OF THE ILLUSTRATIVE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms or definitions are provided solely to aid in the understanding of the invention.

The term "utterance" used herein relates to a complete unit of speech in spoken language. It is generally but not always bounded by silence. It can be represented and delineated in written language in many ways. It is obvious that utterances do not exist in written language, only their representations do.

The term "real-time" relates to hardware or software systems that are subject to a "real-time constraint", for instance operational deadlines from event to system response. As a result real-time programs preferably execute within strict constraints on response time. By contrast a non-real-time system is one for which there is no deadline, even if fast response or high performance is desired or preferred. The need of real-time software is often addressed in the context of real-time operating systems, and synchronous programming languages, which provide frameworks on which to build real-time application software. Real-time computations can be said to have failed if they are not completed before their deadline, whereby their deadline is relative to an event. A real-time deadline must be met, regardless of the system load.

The term "articulator" or "speech organ" relates to organs which can produce the many sounds or utterances needed for language. Organs used include the lips, teeth, tongue, alveolar ridge, hard palate, velum (soft palate), uvula and glottis. Speech organs or articulators can be of two types: passive articulators and active articulators. Passive articulators remain static during the articulation of sound, such as upper lips, teeth, alveolar ridge, hard palate, soft palate, uvula, and pharynx wall, whereas active articulators move relative to these passive articulators to produce various speech sounds, in different manners. The most important active articulators are the tongue, the lower lip and glottis.

Human beings produce utterances via the interaction of the different physiological structures of articulators wherein aerodynamic energy is transformed into acoustic energy. Aerodynamic energy refers to the airflow through the vocal tract. Its potential form is air pressure; its kinetic form is the actual dynamic airflow. The acoustic energy is variation in the air pressure that can be represented as sound waves. Air cavities are containers of air molecules of specific volumes and masses. The main air cavities present in the articulatory system are the supraglottal cavity and the subglottal cavity. They are so-named because the glottis, the openable space between the vocal folds internal to the larynx, separates the two cavities. The supraglottal cavity or the orinasal cavity is divided into an oral subcavity (the cavity from the glottis to the lips excluding the nasal cavity) and a nasal subcavity (the cavity from the velopharyngeal port, which can be closed by raising the velum to the nostrils). The subglottal cavity consists of the trachea and the lungs. The atmosphere external to the articulatory stem may also be consisted an air cavity whose potential connecting points with respect to the body are the nostrils and the lips. When looking at the properties of vowel sounds one can observe a number of properties of vowel sounds which tell us a great deal about how they must be generated. For instance if they have a pitch, they are periodic signals and different vowels have different timbres, so they must have different harmonic amplitudes in their spectra. But if the same vowel can be spoken on different pitches, and different vowels can be spoken on the same pitch, the pitch must be set independently from the vowel quality and if the same vowel can be spoken on different voice qualities, the voice quality must be set independently from the vowel quality. The vowel quality seems to depend mostly on tongue position: front-back and open-close, but vowel quality can also be affected by the position of other articulators, the jaw, lips and velum.

Figure 1A:
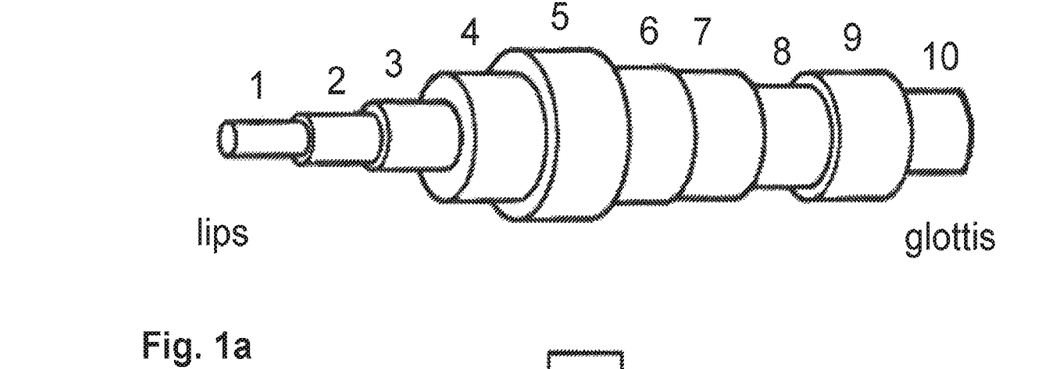
FIG. 1a is a schematic representation of the approximated articulatory model of the vocal tract.
Figure 1B:
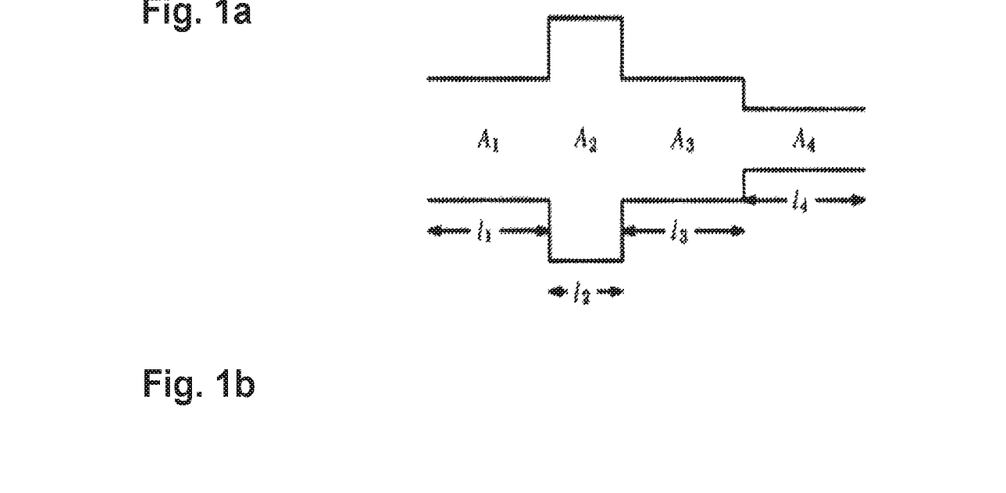
FIG. 1b is a schematic illustration of the approximated articulatory model using a concatenation of four lossless cylindrical acoustic tubes.

All of these above mentioned characteristics of vowels can be analysed, for instance by using models used to describe the production of vowel sounds. One known model which can be used to describe an upper airway or a vocal tract is the approximated articulatory model of the vocal tract illustrated in FIG. 1a. An elementary segment (1, 2, 3, 4, 5, 6, 7, 8, 9 or 10 in FIG. 1a) of the upper airway is represented by a cylindrical tube of a specific length and cross-section area. When a sound wave travels through a series of cylindrical tubes comprising different cross-section areas, the sound wave is partially reflected when crossing from one segment to another. FIG. 1b shows a schematic illustration of the approximated articulatory model using a concatenation of four lossless cylindrical acoustic tubes, each of length and cross-section area A. Thus the upper airway can be viewed as an acoustic tube of varying cross-sectional area terminated by the vocal cords on one end and by the lip opening at the other.

Another model which can be used is the source-filter model of sound production in the upper airway. This model of sound production assumes a source of sound and a filter that shapes that sound, organised so that the source and the filter are independent. This independence allows one to measure and quantify the source separately from the filter. For vowel sounds, the source of sound is the regular vibration of the vocal folds in the larynx and the filter is the whole vocal tract tube between the larynx and the lips. The source-filter model can also be applied to fricative sounds, whereby the source of sound is the turbulence generated by passing air through a constriction, and the filter is the vocal tract tube anterior to the constriction.

It is clear from the above that the spectral characteristics of speech, notably vowels, clearly depend on the anatomical dimensions of a throat. All articulators that contribute to the spectral shaping of an utterance can be described and visualized in real-time for instance by applying a method disclosed by D. Hill et al in Proceedings of AVIOS '95, the 14th Annual International Voice Technologies Applications Conference of the American Voice I/O Society, San Jose Sep. 11-14, 1995, AVIOS: San Jose, pp. 27-44. For the present invention preferably the articulators which influence the cross-section of an airway are determined. More specifically, the geometry of an upper airway is preferably determined using the above mentioned models. Moreover, the present invention can also be applied using natural inhaled/exhaled breathing noise and not only utterance, for instance during sleep or prior to drug inhalation.

Because the upper airway is geometrically very complex and variable in time, establishing a standard operating protocol and understanding of the possible sources of artefacts is of great importance in obtaining reliable results. Of equal importance is the repeatability of measurements obtained to ensure validity of the results.

The invention according to an embodiment relates to a system 10 for characterizing at least one anatomical parameter of an upper airway of a patient, for instance a throat or a vocal tract, by analysing spectral properties of an utterance The invention provides in one embodiment a system for characterizing at least one anatomical parameter of an upper airway of a patient by analysing spectral properties of an utterance, the system comprising:

a mechanical coupler 1 comprising a mouthpiece 11 which restricts the jaw position and which can be anatomically fitted according to the utterance the patient is supposed to perform;

a sound recording unit 2 for recording an utterance, for instance a microphone or the mechanical coupler used as a free-floating microphone; and a computing device preferably comprising a non-transitory memory adapted to determine at least one anatomical parameter of the upper airway from the recorded utterance and comparing the recorded utterance to a threshold value.

Figure 2:
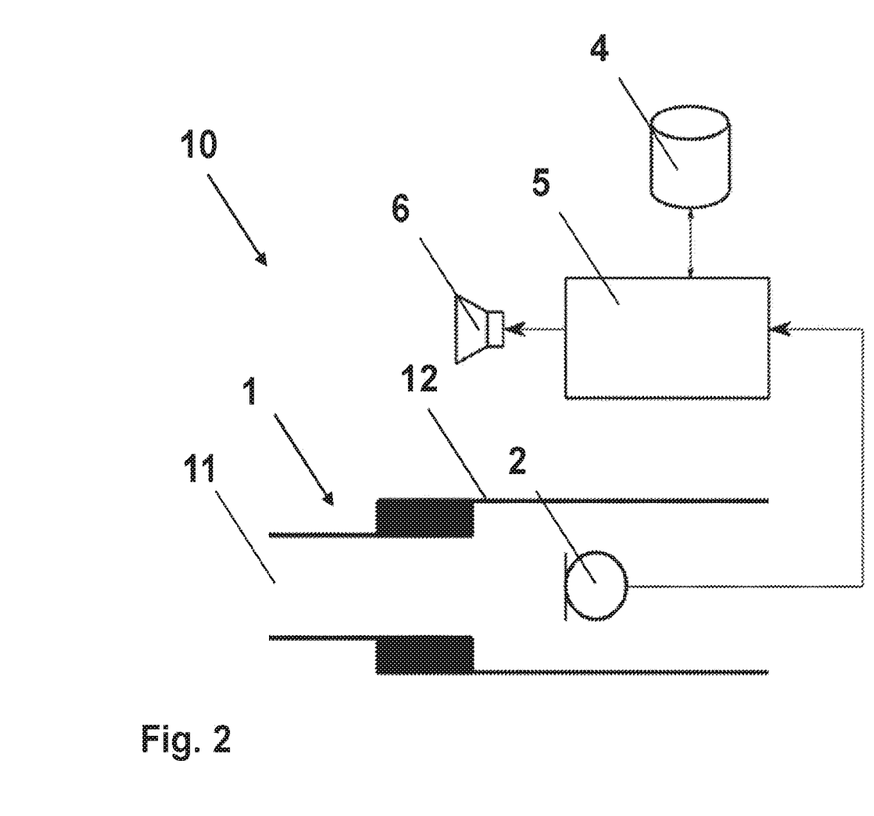
FIG. 2 is a schematic representation of the system according to an embodiment of the present invention.

The system according to an embodiment of the invention is illustrated in FIG. 2. The system comprises a mechanical coupler 1 which is used to transmit a generated audible sound signal, for instance a vocal utterance or a non-vocal utterance, like for instance natural inhaled/exhaled breathing noise, from the to be examined cavity into the system 10. In embodiments of the present invention both vocal and non-vocal utterances can be generated, however vocal utterances may provide less information on the lower airway system as compared to non-vocal utterances. In one embodiment of the invention the mechanical coupler 1 enables the restriction of the jaw position. The latter is in one embodiment of the invention enabled by using different mouthpieces 11 which can be anatomically fitted according to the utterance the patient is supposed to perform. The mouthpiece 11 can ensure, for example, that the teeth and jaws are in a certain position and that the opening of the mouth has a very specific diameter leading to well defined measurement setups. In addition, the mouthpiece 11 can restrict the position of the tongue as well. Advantageously when the jaw position is fixed and the teeth and jaws are in a certain position the opening of the mouth has a very specific diameter leading that the variability in the utterances is reduced and thus enhancing the precision of the measurement.

The mechanical coupler 1 can further comprise a probe 12. The mechanical coupler 1 and, in one embodiment of the invention, the probe 12 can comprise means for recording an utterance, for instance by using a sound recording unit 2 for recording the utterances. In one embodiment of the invention the mechanical coupler 1 and the probe 12 can have a tubular shape but different shapes can be applied as well. In some embodiment, the sound recording unit 2 is integrated with the tube formed by the coupler 1 and the probe 12. This can be enabled for instance by integrating a snoring microphone in an OptiVent In-Line Spacer both developed by Philips Respironics. The setup illustrated in FIG. 2 shows a tubular probe 12 whereby the tubular probe 3 itself can be used as a free-floating microphone 2 without a well defined connection to a user generating the utterances or inhaled/exhaled breathing noise. A free-floating microphone is a microphone where its head has no contact with the damping element or the drum and which is received in a holder. The sound recording unit 2 is in one embodiment of the invention connected to a processing means 5. In another embodiment of the invention the processing means 5 can determine the anatomical parameters of the upper airway from the recorded utterances or inhaled/exhaled breathing noise and compare the determined anatomical parameters to a threshold value. In addition, the processing means 5 can provide feedback in real-time as a result of processing the obtained data in real-time. The processing means 5 can be a computing device comprising in one embodiment of the invention a non-transitory memory. More specifically a personal computer, a laptop, a tablet computer, a smart phone, a mobile phone, a watch or any electronic visual displays which can comprise a touchscreen can be used. In another embodiment of the present invention the processing means 5 can be executed by a single operation for instance with respect to a predetermined button, and hence can be executed by an exceedingly simple operation. All processing means 5 which are known to a person skilled in the art can be used, as well as any software which could enable the characterization of the necessary anatomical parameters can also applied. For instance one can additionally use an adapted version of the EncorePro 2 software by Philips which can display patient compliance data stored by the various element of the system according to the present invention through graphical and statistical analysis. With Encore Pro, a patient's therapeutic history can be maintained and the patient's therapy compliance can be assessed.

The system according to embodiments of the present invention can further comprise means to instruct and control a patient's body position. The upper airway geometry at different body positions (e.g. lying down and standing) can be important to obtain good discriminatory factors between patients suffering from OSA and non-OSA patients. The means to instruct and control a patient's body position can for instance be enabled by adding a 3D accelerometer to the system as illustrated in FIG. 2, which gives the orientation of the system and can be used to instruct and control the patient via the user interface (e.g. the patient could be asked to first do a measurement in standing and then in lying position).

In other embodiments, the processing means 5 can also be connected to a database 4 (locally or remotely) and for instance a loudspeaker, a display or both 6 which can be used as means to provide the feedback to a user. In one embodiment of the invention the display comprises an interface to instruct and provide feedback to the test subject, whereby the usability of the interface is very easy to use by the test subject. In yet another embodiment of the invention the user interface comprises at least one screen, whereby one screen can be a main screen whereas another screen can be used to select a particular parameter, for instance a compression. In addition, many of the functionality's that are important for a good result which can be done autonomously by the device are done by the system itself. An example of this is the determination of the frame rate which is done by determining the number of images in the sequence and the length of the speech fragment and calculating the frame rate using these numbers.

According to some embodiments the database 4 in one embodiment of the invention contains a predefined sequence of utterances that a user can perform. In some embodiments, the database 4 can contain a set of sequences, from which an operator can choose.

In other embodiments, the processing means 5 can for instance be integrated or installed on a mobile device, for instance a mobile phone. In this example, a screen or speaker of the mobile phone can be used as means to provide feedback to a user and accordingly an integrated microphone which is standard on a mobile phone can be used as a sound recording unit. In one embodiment of the invention the mechanical coupler 1 can be a cover that one can attach to the cell phone whereby said cover comprises a tube in front of the microphone. In another embodiment of the invention the tube can be used as means to fix the mount of a user in a predefined way in relation to the integrated microphone. Advantageously, using a mobile phone enables simple and convenient accurate measurements for daytime screening for obstructive sleep apnoea (OSA). In addition, most mobile devices comprise an accelerometer, which would easily be adapted to instruct and control a patient's body position.

The invention according to some embodiments can provide real-time feedback for optimal administration and delivery of respiratory drugs. Knowledge of the upper airway anatomy can improve the proportion of the administered drugs that have to be delivered to a desired location. Drug delivery systems known in the art are not efficient since only about 25% of the administered drug is delivered where it should be, by obtaining real-time feedback on the upper airways one can model the flow of the particles through these upper airways. Knowledge of the upper airway anatomy can improve the proportion of the administered drug that should be delivered to the desired location. In respiratory drug delivery the problem is getting the drug "beyond the throat". Once beyond the throat there are various systemic routes for the drug to reach the targeted alveoli. More drugs delivered "beyond the throat" means a shorter treatment time which is a real differentiator. The means for delivering at least one respiratory drug through the airway of a patient can for instance be an aerosol device, the I-neb AAD system by Philips Respironics which is a fast aerosol generating system can be used. By applying the aerosol technique, a uniform distribution of the drugs with a greater extent of penetration into the peripheral or the alveolar region of the lung can be achieved. The exact dose of the respiratory drugs can be calculated and visualized by applying a flow modelling and based on this the particle delivery is modelled for instance by applying CFD tools like for instance Star CD and Star CCM+ manufactured by CD-adapco. More specifically the particle delivery and the timing of the aerosol generation can be optimized and in this way the drug delivery can be personalized but restricted by the medication prescription. In some embodiments of the invention the cross-section of the upper airway is determined by the processing means 5 and in addition a point in time when the cross-section is maximal during an utterance can be determined. This point of time when the cross-section of the upper airway is maximal, can be used for the timing of the aerosol generation, which then can be optimized for drug delivery, thus providing a system tuning approach. In addition a mechanical coupler restricting the jaw position, for instance by applying a stepped-mouthpiece (K. Nikander et al in "Manipulation of upper airway volume using a stepped mouthpiece" ERS, September 2010) can be used as a way to force the upper airways to open up. Feedback to the patient on the way his/hers upper airway is opened up is beneficial to this goal. In addition it may support adherence and compliance. Advantageously embodiments of the present invention enable the amount of drug delivery to be more controllable, consistent and repeatable over the various therapy sessions.

Figure 3:
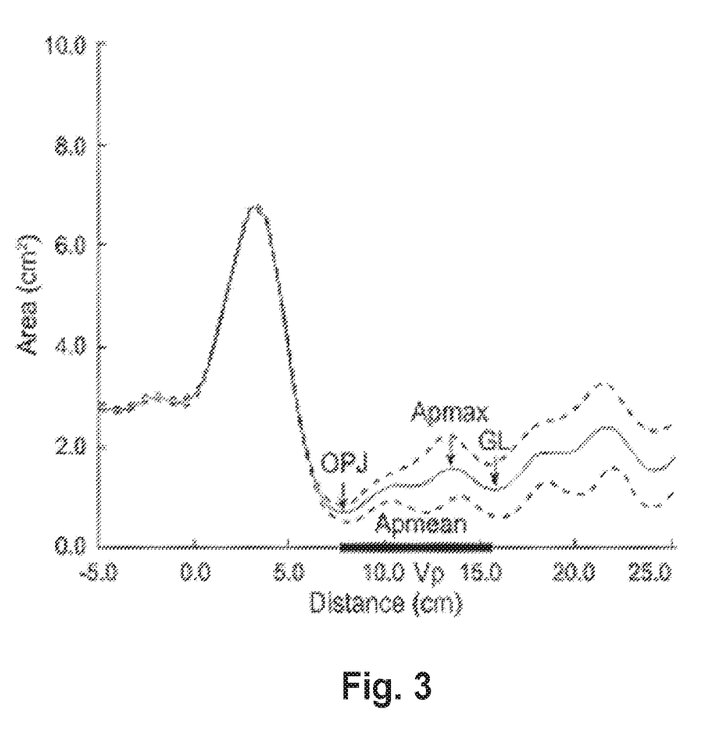
FIG. 3 illustrates a representative output of an acoustic pharyngometry measurement.

A method according to an embodiment of the invention can comprise one of the following steps: the system tells the patient which utterance to perform, which the system records. In a next step a processing means 5 performs can check on the correctness of the recorded utterance, for example by means of speech recognition to determine whether the correct utterance has been performed. Several speech recognition models known in the art can be used to enable the latter, for instance by applying a vector Taylor series approach for environment-independent recognition, or by using a parallel model combination (PMC) scheme, or hidden Markov models. If the utterance was not correct, the system can ask the patient to repeat it. In a next step the system can repeat the previous steps until all predefined utterances have been performed correctly by the patient. The processing means can then extract and analyse the features important for OSA diagnosis. An example of a method which can be used is disclosed by Robb et al in *Vocal tract resonance characteristics of adults with obstructive sleep apnoea* in Acta Otolaryngology, 1997. 117(5): p. 760-3. Or as an alternative embodiment the following steps can be applied: spectral properties of the utterances can be analysed, resulting in a determination of the anatomical parameters of the upper airway, for instance dimensions of the throat between the vocal chords and the mouth. In one embodiment of the invention the derived dimensions can be used as an indicator for OSA. In other embodiments the dimensions can be linked to other measurements for which the predictive power has already been established, for instance measurement data of an acoustic pharyngometry measurement as illustrated in FIG. 3. FIG. 3, taken from Jung et al. shows the representative output of an acoustic pharyngometry measurement, having the parameter area on the Y-axis and the parameter distance on the X-axis. One can distinguish 5 parameters on the graph (as emphasized by arrows and a thick line): (1) oropharyngeal junction area (OPJ), (2) Apmax, the maximum pharyngeal area, (3) glottis area (GL), (4) Apmean the mean pharyngeal area from OPJ to GL and (5) Vp, the pharyngeal volume as the integrated area under the curve between the OPJ and the GL. All the parameters can be calculated by for instance the processing means according to embodiments of the present invention.

Figure 4A:
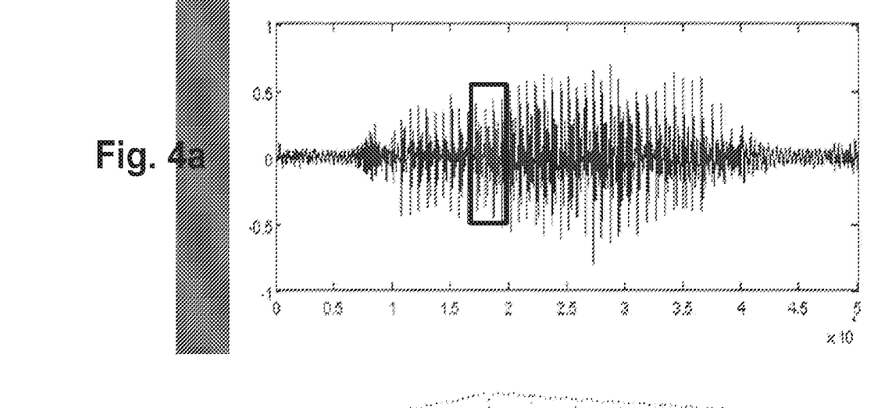
FIG. 4a and FIG. 4b illustrate a real time estimation of upper airway tract based on uttered sounds using a system according to an embodiment of the present invention.
Figure 4B:
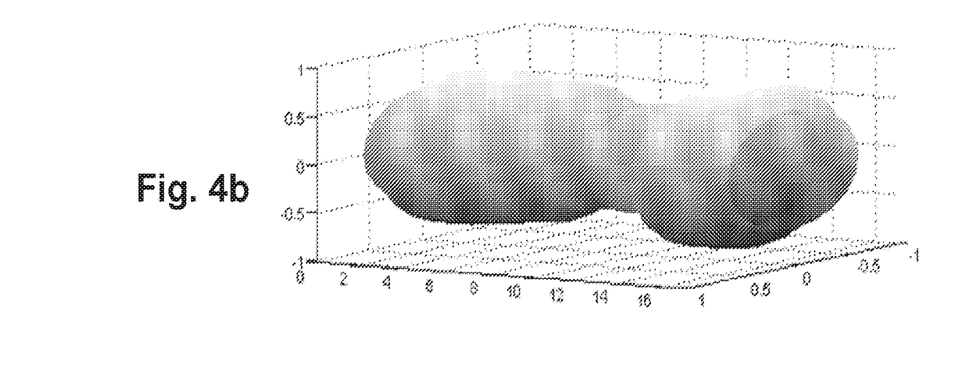

Alternatively, the values can also be linked to the presence of OSA in a trial that is run specifically for derivation of a detector based on speech features. Another method to derive the cross-sectional dimensions from the lips to the glottis is by applying a speech-coding by for instance Linear Predictive Coding (LPC). LPC has can be implemented to model the human vocal tract. This method can also be used for obtaining a real-time estimate of the instantaneous throat geometry for optimizing respiratory drug delivery in terms of more efficient deposition and shorter treatment times as illustrated in FIGS. 4a and 4b. Embodiments of the present invention provide feedback to the patient while he/she holds its throat open by uttering sounds, e.g. exhaling. In a subsequent inhale, while keeping the throat fixated, the drug delivery can take place. Direct feedback can improve adherence and compliance.

In some embodiments of the invention the determined values can be compared to predefined thresholds or used by a more sophisticated classifier to give a probability that the patient is suffering from OSA as illustrated in FIGS. 4a and 4b. The result can be given to an operator. An example of a classifier is for instance the naïve Bayesian classifier known in the art. The classifier can also include physiological measures such as BMI and neck circumference to increase screening performance. The present invention can additional be applied for OSA phenotyping. The throat dimensions obtained from the processing means can help to identify different types of OSA, providing an indication for the most successful treatment (CPAP, surgery).

An alternative embodiment of the present invention is a system comprising a training mode. The training mode can be applied to two groups of patients, one group diagnosed with OSA and another group diagnosed non-OSA. When the two groups are examined, reference data can be obtained which can then be used in future measurements. The processor then autonomously can train the implemented classifier to be used for future tests.

In yet another embodiment the system is not only used for a one-time measurement but used in repeating check-ups. To this end a patient's results can be stored in a database (locally or remotely, not necessarily identical with the previously mentioned database). The next time the patient receives a check-up the system can be used to record another measurement. This can then be compared to the previous results of this patient. This decreases the importance of absolute numbers obtained during a one-time measurement and enables the observation and evaluation of a trend. To simplify the comparison of several measurements the system can be equipped with a state-of-the-art speaker-recognition module. It autonomously can assign new measurements to previous measurements by identifying the speaker based on the performed utterances.

Other arrangements for accomplishing the objectives of the device embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A system for characterizing at least one anatomical parameter of an upper airway of a patient based on an utterance in the form of a complete unit of speech in spoken language generated by the patient, comprising: a mechanical coupler structured to fix a position of a jaw and teeth of the patient and cause a mouth of the patient to have a predetermined diameter while the patient is generating the generated utterance and transmit an audible sound signal comprising the generated utterance; a sound recording unit structured to receive the audible sound signal from the mechanical coupler and generate a recording of the audible sound signal; and a computing device structured and configured to: (i) receive the recording of the audible sound signal, (ii) determine, from the recording of the audible sound signal, a correctness of the generated utterance as compared to and as matching a predetermined utterance in the form of a complete unit of speech in spoken language to be performed by comparing the complete unit of speech of the generated utterance to the complete unit of speech of the predetermined utterance, and (iii) responsive to a determination that the complete unit of speech of the generated utterance matches the complete unit of speech of the predetermined utterance, determine at least one anatomical parameter of the upper airway based on the recording of the audible signal by extracting and analyzing spectral properties of the generated utterance from the recording of the audible signal.

2. The system according to claim 1 whereby said computing device is structured and configured to provide real-time feedback based on the at least one anatomical parameter.

3. The system according to claim 1, wherein the computing device is further structured and configured to determine the correctness of the generated utterance using speech recognition, and responsive to determining that the generated utterance is not correct, instructing the patient to repeat the utterance.

* * * * *